(12) United States Patent
Peel

(10) Patent No.: US 6,673,030 B1
(45) Date of Patent: Jan. 6, 2004

(54) CASTING MATERIAL

(75) Inventor: Claire Peel, Murton (GB)

(73) Assignee: BSN Medical, Inc., Wilmington, DE (US)

( * ) Notice: Subject to any disclaimer, the term of this patent is extended or adjusted under 35 U.S.C. 154(b) by 0 days.

(21) Appl. No.: 09/868,192

(22) PCT Filed: Dec. 16, 1998

(86) PCT No.: PCT/GB98/03724
§ 371 (c)(1),
(2), (4) Date: Feb. 11, 2002

(87) PCT Pub. No.: WO00/35501
PCT Pub. Date: Jun. 22, 2000

(51) Int. Cl.[7] .................................................. A61F 5/00
(52) U.S. Cl. .................... 602/6; 602/5; 602/8; 602/19
(58) Field of Search ................................ 602/1, 5, 6, 8, 602/19, 60

(56) References Cited

U.S. PATENT DOCUMENTS

| 2,198,776 A | * | 4/1940 | King et al. |
| 2,960,984 A | | 11/1960 | Parker |
| 3,770,468 A | * | 11/1973 | Knauf et al. |
| 3,785,479 A | | 1/1974 | Smith |
| 3,923,049 A | | 12/1975 | Lauber et al. |
| 4,136,687 A | | 1/1979 | Dabroski |
| 4,235,228 A | | 11/1980 | Gaylord, Jr. et al. |
| 4,362,762 A | | 12/1982 | Lindquist et al. |
| 4,454,874 A | | 6/1984 | Monnier |
| 4,942,003 A | * | 7/1990 | Bold |
| 5,027,803 A | | 7/1991 | Scholz et al. |
| 5,713,838 A | | 2/1998 | Termanini |

FOREIGN PATENT DOCUMENTS

| GB | 807406 | | 1/1959 |
| GB | 859018 | | 1/1961 |
| GB | 2 082 461 A | | 3/1982 |
| JP | 410158050 A | * | 6/1998 |
| WO | WO 90/02538 | | 3/1990 |
| WO | WO 99/11300 | | 3/1999 |

* cited by examiner

Primary Examiner—Nicholas D. Lucchesi
Assistant Examiner—Lalita M. Hamilton
(74) Attorney, Agent, or Firm—Adams Evans P.A.

(57) ABSTRACT

An Orthopaedic Plaster of Paris bandage (10) comprising a water resistant layer of material (50; 60) on at least one face of the bandage (10) which allows the bandage (10) to be cured by water but once the bandage (10) is set, the bandage (10) is water resistant against disintegration.

15 Claims, 2 Drawing Sheets

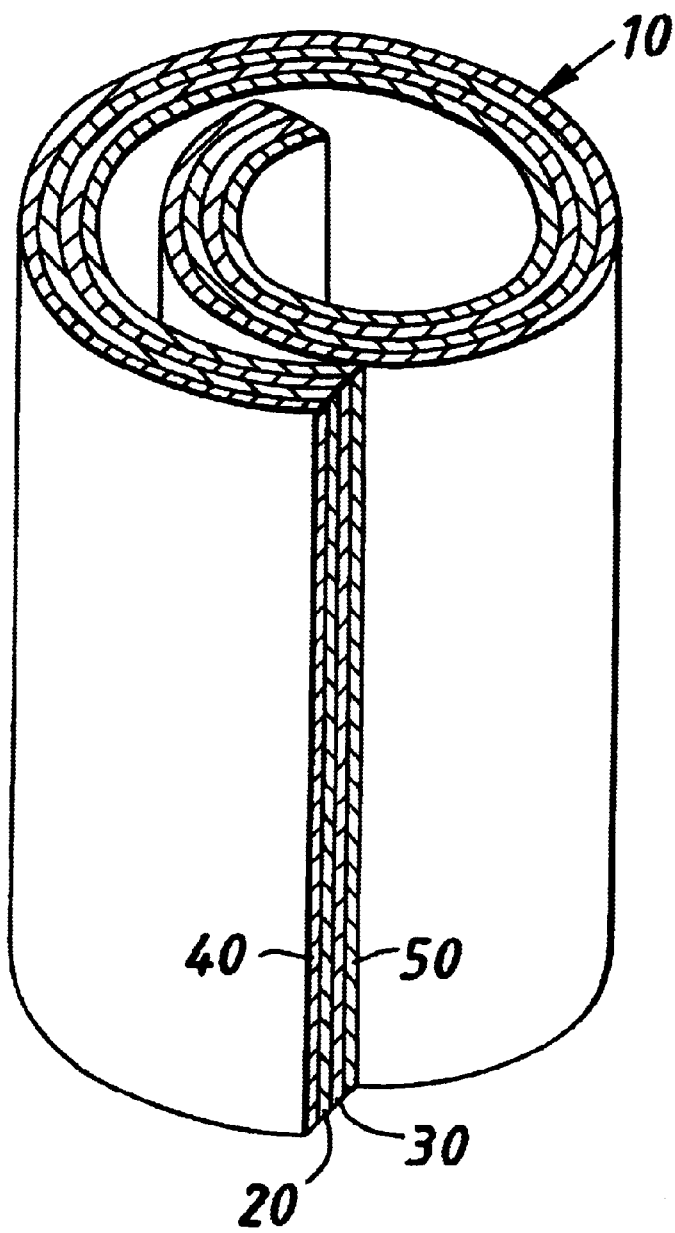
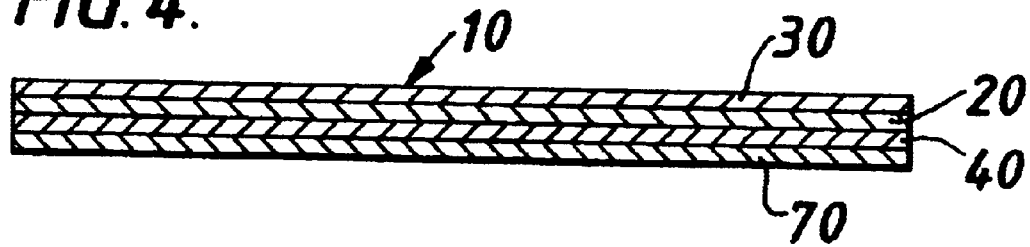

CASTING MATERIAL

This application is a national stage application, according to Chapter II of the Patent Cooperation Treaty. This application claims the priority date of Dec. 16, 1998 for International Patent Application No. PCT/GB98/03724.

Plaster of Paris bandages are well known in the art and are generally employed for arthopaedic applications such as casting and splinting.

Plaster of Paris casts however are sensitive to water and patients wearing Plaster of Paris casts have to avoid rain and can not shower.

Polyurethane resin based casts have to some extent alleviated this problem as they are waterproof, however their cost is prohibitively expensive for many people. It is also an advantage to still use Plaster of Paris casts when the injured limb being protected by the casts is likely to swell as a Plaster of Paris cast can be disintegrated by submerging in water.

Thus it is desirable to develop a water resistant Plaster of Paris cast or splint that would overcome or at least inhibit disintegration of the Plaster of Paris in damp or wet conditions.

In the prior art many solutions have been sought, such as painting the cast after application to a patient with a waterproofing material. This however involves a second step.

The addition of a water resistant agent to the Plaster of Paris during the manufacturing process was previously anticipated that it would interfere with the adhesion of the Plaster of Paris to the substrate and also with the setting process of the Plaster of Paris.

Surprisingly we have found however that the application of a thin water resistant film on at least one side of the bandage results in a material that can be wetted as well as resulting in a water resistant cast on application.

It had been previously thought that on applying a water resistant film to the bandage, that this would prevent or inhibit the bandage from being wetted out in order to cure the Plaster of Paris and thus it would be unable to apply the bandage to a patient.

It was also believed that using a fluid vehicle that contained water to apply the water resistant layer would cause premature curing of the cast. The present invention has surprisingly found that using a fluid vehicle that does contain water may not cause significant premature curing of the bandage when applied according to the present invention.

According to the present invention there is provided a Plaster of Paris splint bandage comprising a flexible substrate carrying the hemi-hydrate form of calcium sulphate characterised by that the bandage has a layer of water resistant material which allows the bandage to be cured but when the bandage is set provides water resistance.

The materials referred to as water resistant materials, or as water resistant agents, are defined as materials which when on the Plaster of Paris splint bandage will allow water to penetrate the water resistant material in order to cure the bandage but when the bandage is set will offer some degree of water resistance to the cured bandage.

Also according to the present invention there is provided a Plaster of Paris splint bandage comprising a flexible substrate carrying Plaster of Paris with an upper face and a lower face, wherein at least one of the upper face or the lower face comprises a layer of water resistant material.

The upper face is defined as the side facing away from the limb after application and the lower face is defined as the body facing side of the bandage.

Preferably the water resistant material is applied after the substrate is impregnated with Plaster of Paris. Further for ease of manufacture and use, it is preferred that the water resistant material is applied after the substrate is impregnated with Plaster of Paris but before curing and application of the bandage.

For further ease of applying the water resistant agent, or material, onto the bandage it is convenient if the water resistant material is a fluid, or is contained in a fluid, to give a fluid vehicle in order to allow convenient application of the water resistant material onto the bandage. Used herein the fluid vehicle is the water resistant material in fluid form or any fluid containing the water resistant material.

The fluid vehicle carrying the water resistant material may be applied to the cured bandage after application to a patient but preferably the fluid vehicle carrying the water resistant material is applied during the manufacturing process.

Most aptly the fluid vehicle is sprayed onto the upper face during the manufacturing process, thus providing a layer of a water resistant material. However any method suitable for the application of the fluid vehicle may be used, for example the bandage could be dipped into the fluid vehicle.

The fluid vehicle carrying the water resistant material may be applied to one surface or face of the bandage, either the upper face or the lower face, or may be applied to both faces of the bandage.

Provided that the fluid vehicle can form a layer of the water resistant material on, or within, the bandage, the water resistant material does not necessarily need to be applied to the outer layer of the bandage. Preferably however, the water resistant layer will be on an outer surface or face of the bandage.

The water resistant material is aptly applied neat, i.e. undiluted especially if a fluid for example silane, or in the form of an emulsion, solution, mixture or suspension. The fluid vehicle may consist wholly or partially of the water resistant material.

Any fluid vehicle, suitable to apply the water resistant material on to one or more of the surfaces of the bandage, could in fact be used. The fluid vehicle may be water based, solvent based or a mixture thereof. This would include suspensions and emulsions.

When the fluid vehicle is an emulsion or solution, the emulsion or solution may be prepared from any material that will form an emulsion or solution and which forms a water resistant film on drying after application of the bandage to a limb.

Typically the water resistant material may be in the form of an emulsion, solution or suspension in water. When a solvent is used suitable ratios of solute to solvent are typically 25% to 75%. Suitable solvents that may be used with the present invention include alcohols, ketones, aromatic hydrocarbons, aliphatic hydrocarbons, esters and ethers.

If the water resistant film is only on one side or face of the bandage the opposite face would comprise exposed Plaster of Paris. This enables the Plaster of Paris to wet out quickly, as well as enabling lamination of the layers and smoothing out of the resulting cast.

If the water resistant film is on both sides it is preferable to have a lower individual layer weight of the water resistant material than that used on a bandage with only one layer of the water resistant material. This is to enable the water to migrate through the film more efficiently and this enables the Plaster of Paris to wet out quickly, as well as enabling lamination of the layers and smoothing out of the resulting cast.

On application a water resistant upper face will preferably make up the outside of the cast, thus resulting in a water resistant cast.

Suitably the water resistant layer comprises 1 to 25% by cast weight. The water resistant layer need not be a thick layer provided it can offer water resistance to the bandage and therefore this layer may be less than 1% of the weight of the cast.

Water resistant bandages according to the present invention could be used for the entire cast or just to provide a layer of the water resistant material on, or within, the cast. Therefore water resistant bandages of the present invention could be used in conjunction with ordinary bandages. It is envisaged that where water resistant bandages of the present invention are used in conjunction with ordinary bandages, the water resistant bandages will be applied as a last layer, or outer layer, of the bandaging material making up the cast in order to give an outer water resistant layer of material to protect the cast as a whole. In this way the ordinary bandages can be used to provide a cast of the required thickness or strength, while the water resistant bandages of the present invention provide water resistance to the cast.

Suitably when the fluid vehicle used contains water it will contain an amount of water less than the stoichiometric amount of water required to convert the hemi-hydrate to dihydrate of the Plaster of Paris bandage. Where the fluid vehicle contains water it is preferred that the amount of water used is less than 0.5 mole of water per mole of hemi-hydrate calcium sulphate used in the bandage. Preferably around 0.2 of water per mole of hemi-hydrate calcium hydrate used in the bandage, would be used where the fluid vehicle contains water.

It is still possible to apply the water resistant material when much larger amounts of water, than described above, are used in the fluid vehicle to apply the water resistant layer by heating the bandage to around 100° C., or above, and applying the fluid vehicle to the heated bandage. The water resistant material can then be applied to the surface of the bandage while the water evaporates off before causing significant curing of the bandage.

It is even possible to use copious amounts of water to apply the fluid vehicle which if did cure the bandage could be heated to a temperature sufficient enough to convert the di-hydrate form of Plaster of Paris to the hemi-hydrate form.

Once the water resistant material is applied to the bandage the treated bandage, comprising at least one layer of a water resistant material, can be used before the layer of water resistant material has dried onto the bandage. It does not necessarily matter if the layer of water resistant material, on or within, the bandage has not dried completely before the bandage is immersed in water to initiate curing. Alternatively the bandage comprising a layer of water resistant material can be allowed to dry completely, and stored, before being applied to a user in the usual method of applying Plaster of Paris bandages. The bandage according to the present invention can thus be supplied to the user with the layer of water resistant material dry or wet.

Where bandages of the present invention are to be applied where the layer of water resistant material on the bandage is still wet or at least not completely dry, the bandage may be placed in a fluid, or moisture, impermeable container before the layer of water resistant material on the bandage is able to completely dry. The bandage may then be stored in the container in this wet form, or embodiment of the present invention, ready to be applied to a user in the usual method. The water penetration of the bandage during the curing process may also be made more efficient by having a wet layer of water resistant material. Applying a bandage with a wet layer of water resistant material may also assist with the drying of the bandage after curing.

Suitable material for the impermeable container may be any conventional material, for example, plastic film paper product, metallic foil, laminates or any other material which will be impermeable to fluids.

The container may be of any size and shape which is able to contain the required contents. Suitable packaging to act as the container are 3 dimensional bags well known in the art.

The water resistant material may be any material capable of forming a water resistant layer on, or within, the bandage. Typically the water resistant material will be a readily available water resistant agent or polymer.

Any suitable water resistant agent can be used, for example silicones, polyvinylchlorides, alkoxysilane resins, hydrocarbon waxes or preferably polyvinyl acetate/acrylic acid copolymers.

Coloured dye may also be added to the fluid vehicle to produce a finished cast of a chosen colour whereby the dye may be trapped in a film layer of the bandage. Any dye suitable to dye the finished cast may be used. Both water soluble and water insoluble dyes could be used. Alternatively the dye need not be added to the fluid vehicle but may be added at any other appropriate time to produce a dyed finished cast.

Water resistant Plaster of Paris splint bandages according to the invention can be factory manufactured and supplied to the user in a ready to use form whether the water resistant material on the bandage is dry or wet. When the water resistant splint bandage is factory manufactured and supplied to a user with a wet layer of the water resistant material it is envisaged that the bandage with its wet layer of water resistant material will be contained in a fluid impermeable container at the manufacturing stage, ready for use.

Alternatively kits to produce a water resistant Plaster of Paris splint bandage from an ordinary Plaster of Paris bandage supplied with the kit, or not, can be manufactured and supplied to the user. The kits will contain a water resistant material to be applied to an ordinary Plaster of Paris bandage, whether this is itself supplied with the kit or not, for application to the ordinary Plaster of Paris bandage to produce a water resistant Plaster of Paris splint bandage of the present invention. On using the water resistant Plaster of Paris splint bandage kit, the user can decide if the water resistant material applied to the bandage is to be used wet or dry. If it is to be used wet it may be used immediately or could be store in a fluid impermeable container. If the bandage is to used with a dry layer of water resistant material, the bandage will be required to be dried before use.

The invention will now be described by way of example only with reference to the accompanying drawings.

FIG. 3 shows the bandage of FIG. 1 in rolled up form.

FIG. 4 shows a cross section of the Plaster of Paris splint bandage of a further embodiment of the invention.

Figure 1:
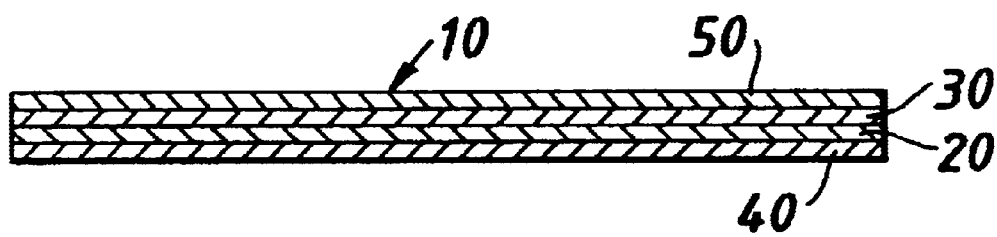
FIG. 1 shows a cross section of a Plaster of Paris splint bandage of the invention.

FIG. 1 shows a Plaster of Paris splint bandage 10 comprising a substrate 20 impregnated with Plaster of Paris resulting in a layer of Plaster of Paris on the upper face 30 and lower face 40. The upper face 30 additionally has a water resistant layer 50.

Figure 2:
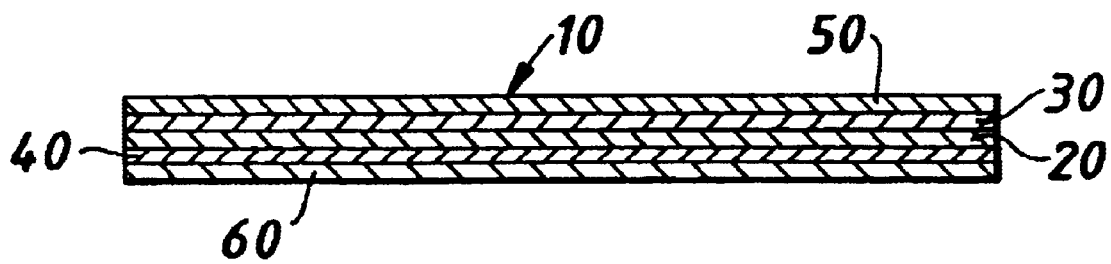
FIG. 2 shows a cross section of the Plaster of Paris splint bandage of a further embodiment of the invention.

FIG. 2 shows a Plaster of Paris splint bandage 10 of FIG. 1 comprising a substrate 20 impregnated with Plaster of Paris resulting in a layer of Plaster of Paris on the upper face 30 and lower face 40. The upper face 30 and lower face 40 additionally have a water resistant layer 50 and 60.

FIG. 3 shows the bandage 10 in a rolled up form. The bandage can be rolled with either face on the outside, depending on the application techniques used by casting technicians.

FIG. 4 shows a Plaster of Paris splint bandage 10 of FIG. 1 comprising a substrate 20 impregnated with Plaster of Paris resulting in a layer of Plaster of Paris on the upper face 30 and lower face 40. The lower face 40 additionally has a water resistant layer 70.

The invention will be further illustrated by the following further examples.

Bandages

Bandages containing various water resistant agents were tested for their water resistance determined by measuring their Breaking Load after water was applied to the surface of the bandage in comparison to controls.

Plaster of Paris bandages sold under the Smith & Nephew Trade Mark GYPSONA were used. The bandages used were 6.1 m in length and 10 cm wide (0.16 $m^2$).

The coating weight of plaster mass on the substrate was approximately between 390 to 560 grams per square meter. The substrate is leno gauze as supplied by Smith & Nephew Medical Fabrics.

All bandages were prepared by unspooling the bandage cutting to the desired length and then respooling onto a core, then stored in a resealable bag until needed. Bandages were weighed without the core before being treated, and then were treated by applying the water resistant agent to either the upper face only of the bandage or the lower face. After the water resistant material has been applied to the bandages, the bandages were reweighed to calculate the weight of the water resistant material.

Preparation of Water Resistant Agent

Unless commercially bought in a ready to use form the fluid vehicle whether this was water based or solvent based or a mixture thereof was heated and agitated using a hot plate stirrer. When a water resistant agent requiring dissolving was used it was first dissolved into the fluid vehicle. The required amount of water resistant agent was added slowly to the fluid vehicle, avoiding agglomeration. When the water resistant agent was dissolved the solution was allowed to cool to room temperature and then made up to volume before being stored at room temperature until required.

Water Resistance of Test Samples

Different water resistant agents were tested by spray application with a pressure range from 17 psi to 60 psi. The spray gun was held approximately 5 cm in distance from the bandage when applying the water resistance agent. The amount of water resistant agent and amount of coverage was as follows.

(1) One Face of Bandage Having the Dry Water Resistant Layer

The bandage was unspooled, the fluid vehicle containing the water resistant agent was then evenly sprayed onto the whole bandage on one side and was then left to dry. After drying the sample bandage was weighed and then spooled on to a core and stored in a resealable bag until required.

Bandages prepared in this way could be used when the water resistant layer was on the inner face or the outer face of the bandage depending on which way round the bandage was applied.

(2) One Face of Bandage Having the Wet Water Resistant Layer

The bandage was unspooled, the fluid vehicle containing the water resistant agent was then evenly sprayed onto the whole bandage on one side, the upper face. The treated bandage was weighed and immediately spooled on to a core and stored in a resealable bag, before drying, until it was required.

Preparation of Casts

The treated bandages, having at least one layer of a water resistant material, stored in resealable bags were immersed in a large excess of water for around 6 seconds and squeezed once on removal to remove excess water.

Once the curing process of the bandage had been initiated the roll of bandage was formed into a 5 cm diameter by 10 cm wide cast by, unrolling the bandage around a 5 cm diameter cylinder (mandrel). When the bandage had been unwound the final layer was smoothed until initial setting occurred. The bandage was then removed from the mandrel and placed at room temperature to dry for at least three days.

Treated bandages with the upper face having a water resistant layer were used as a last layer only on preparing some sample casts. These sample casts were prepared using 1.4 m length of untreated bandage for the inner layers of the cast and 0.2 m length of the treated bandages, for the last outer layer (with overlap). These casts were, similarly, removed from the mandrel and placed at room temperature to dry for at least three days.

Water Resistance Testing of Casts

Cast samples were prepared as described above and then tested for wet strength using a "drip test". The "drip test" is defined by marking the cast to be tested at 90° intervals and then suspending this cast so that water would drip onto the cast (to mimic a shower). The sample cast being tested was rotated by 90° each minute, for eight minutes, to insure an even wetting of the sample while water was dripped onto the cast at a rate of 60 ml/minute. After the test period excess water was removed from the cast using absorbent paper and then the sample cast was tested for its breaking load, under the "crush test".

The "crush test" is defined as follows. Using a Zwick 1464 machine the breaking load required to reach the yield point of the cast sample was determined. The samples were loaded diametrically and then compressed by 8 mm. The Load Cell used was 50 kN and the test speed was 5 mm/min.

Controls

Untreated bandages were cured and applied to 5 cm diameter Mandrels to form a control cast in a similar way as for the treated bandages. These untreated casts were tested for their breaking load after the drip test in order to give a comparison of breaking load.

| Water Resistant Agents used | | | |
|---|---|---|---|
| Trade Name | Chemical Name | Abbreviation | Supplier |
| Thompsons All-purpose Wood Preserver | Mixture including an organotin PVC stabiliser | (WP) | |
| Yacht Varnish | Oil Modified polyester | (PE) | |
| X935-19 | | (ICI) | ICI Paints Division Middlesborough |
| Vernish Fisch | | (VF) | S & N Lab. Fisch |
| — | silane resin | | S & N GRC |
| Blackfriar Quick Drying Interior Varnish | | (IV) | |
| PVP K15 | Poly(vinyl | (PVP) | International |

-continued

Water Resistant Agents used

| Trade Name | Chemical Name | Abbreviation | Supplier |
|---|---|---|---|
| | pyrrolidone) | | Speciality Products |
| PVA GL05 | Poly(vinyl alcohol) | (PVA) | Nippon Gohshei |
| Emultex 592 | Polyvinyl acetate/acrylic copolymer | | Harco Chemical Co. |

EXAMPLES

Each sample was tested under the above conditions.

| Example | Water Resistant Material | Amount (g) | Breaking Load Improvement |
|---|---|---|---|
| Dry Water Resistant Material on Upper Face of Bandage. | | | |
| 1 | ICI | 3.7 | 30 |
| 2 | ICI | 6.7 | 32 |
| 3 | ICI | 6.3 | 28 |
| 4 | IV | 3.6 | 16 |
| 5 | Silane | 0.7 | 27 |
| 6 | PE | 0.6 | 14 |
| Dry Water Resistant Material on Lower Face of Bandage | | | |
| 7 | ICI | 2.6 | 11 |
| Dry Water Resistant Material on Upper Face of Bandage and Treated Bandage used for last layer only. | | | |
| 8 | ICI | 24.3 | 69 |
| 9 | PVP | 19.5 | 24 |
| 10 | IV | 0.8 | 16 |
| 11 | PE | 2.1 | 36 |
| 12 | WP | 15.1 | 27 |
| Wet Layer of Water Resistant Material on Upper Face of Bandage. | | | |
| 13 | 50% VF | 7.7 | 21.5 |
| 14 | WP | 0.66 | 10 |

Example 15

An emulsion of polyvinyl acetatelacrylic acid copolymer, available as a 50% solids in emulsion sample (Emultex 592) from Chemical Co. was used.

A Plaster of Paris bandage comprising a leno gauze substrate impregnated with Plaster of Paris was laid out flat and sprayed on one side with the emulsion. After drying the bandage was rolled up with the layer of water resistant material on the inside.

For application the bandage was applied using a standard technique of dipping the rolled-up bandage into water, squeeze once and applying the bandage to a mandrel representing a limb.

In this way a water resistant splint bandage was produced.

What is claimed is:

1. A Plaster of Paris splint bandage, comprising:
   (a) a flexible substrate;
   (b) a hemi-hydrate form of calcium sulfate carried by said substrate, said hemi-hydrate form of calcium sulfate remaining stable when maintained in moisture-free conditions and curing upon exposure to sufficient moisture to form a rigid, self-supporting structure; and
   (c) a layer of water resistant material carried by said bandage, said water resistant material permitting subsequent exposure of the hemi-hydrate form of calcium sulfate to the moisture used to initiate curing while providing water resistance to the bandage after curing is complete, said water resistant material being contained in a fluid vehicle, wherein said fluid vehicle contains a predetermined amount of water less than the stoichiometric amount of water required to convert the hemi-hydrate form of calcium sulphate in the bandage to the dy-hydrate form of calcium sulphate.

2. A Plaster of Paris splint bandage according to claim 1, wherein the layer of water resistant material is wet on the bandage.

3. A Plaster of Paris splint bandage according to claim 1, wherein the bandage is stored ready for use in a fluid impermeable container.

4. A Plaster of Paris splint bandage according to claim 1, wherein said fluid vehicle is selected from the group consisting of a second water resistant material, a water based fluid, a solvent based fluid, and a mixture of water and solvent.

5. A Plaster of Paris splint bandage according to claim 1 wherein said predetermined amount of water comprises less than 0.5 mole of water per mole of the hemi-hydrate form of calcium sulphate used in the bandage.

6. A Plaster of Paris splint bandage according to claim 1, and including a dye carried by the bandage for imparting color thereto.

7. A Plaster of Paris splint bandage according to claim 1, wherein said fluid vehicle includes a dye for imparting color to the bandage.

8. A Plaster of Paris splint bandage according to claim 1, wherein the water resistant material comprises between 1 and 25 percent of the total weight of the bandage.

9. A Plaster of Paris splint bandage according to claim 1, wherein the water resistant material comprises a polymer selected from the group consisting of Poly(vinyl pyrrolidone) and Poly(vinyl acetate).

10. A method of manufacture of a water resistant Plaster of Paris splint bandage, comprising the steps of:
   (a) providing a bandage including a flexible substrate carrying a hemi-hydrate form of calcium sulfate thereon, said hemi-hydrate calcium sulfate remaining stable when maintained in moisture-free conditions and curing upon exposure to sufficient moisture to form a rigid, self-supporting structure; and
   (b) applying a layer of water resistant material to said bandage prior to exposure of the hemi-hydrate form of calcium sulfate to the moisture to initiate curing thereof, said water resistant material imparting water resistance to the bandage after curing is complete, said water resistant material being contained in a fluid vehicle, wherein said fluid vehicle contains a predetermined amount of water less than the stoichiometric amount of water required to convert hemi-hydrate form of calcium sulphate in the bandage to the di-hydrate form of calcium sulphate.

11. A water resistant splint bandaging system, comprising:
   (a) a Plaster of Paris splint bandage carrying a hemi-hydrate form of calcium sulfate thereon adapted for remaining stable when maintained in moisture-free conditions and curing upon exposure to sufficient moisture to form a rigid, self-supporting structure; and (b) a water resistant material for being applied in a layer to said bandage prior to exposure of the bandage to the moisture, said water resistant material imparting water resistance to the bandage after curing is complete, said water resistant material being contained in a fluid vehicle, wherein said fluid vehicle contains a predetermined amount of water less than the stoichiometric amount of water required to convert the hemi-hydrate form of calcium sulphate in the bandage to the di-hydrate form of calcium sulphate.

12. A water resistant splint bandaging system according to claim 11, wherein the water resistant material is contained in a spray.

13. A water resistant splint bandaging system according to claim 11, wherein the water resistant material comprises a polymer selected from the group consisting of Poly(vinyl pyrrolidone) and Poly(vinyl acetate).

14. A water resistant splint bandaging system according to claim 11, wherein the water resistant material comprises between 1 and 25 percent of the total weight of the bandage.

15. A water resistant splint bandaging system according to claim 11, and including a dye carried by the bandage for imparting color to the bandage.

* * * * *